United States Patent [19]
Sata

[11] Patent Number: 5,412,702
[45] Date of Patent: *May 2, 1995

[54] X-RAY COMPUTERIZED TOMOGRAPHIC IMAGING METHOD AND IMAGING SYSTEM CAPABLE OF FORMING SCANOGRAM DATA FROM HELICALLY SCANNED DATA

[75] Inventor: Shingo Sata, Tochigiken, Japan

[73] Assignee: Kabushiki Kaisha Toshiba, Kanagawa, Japan

[ * ] Notice: The portion of the term of this patent subsequent to Jun. 8, 2010 has been disclaimed.

[21] Appl. No.: 943,544

[22] Filed: Sep. 11, 1992

[30] Foreign Application Priority Data

Sep. 12, 1991 [JP] Japan .................. 3-232688

[51] Int. Cl.$^6$ .............................. G01N 23/00
[52] U.S. Cl. ............................ 378/4; 378/20
[58] Field of Search ...................... 378/4–20

[56] References Cited

U.S. PATENT DOCUMENTS 4,630,202 12/1986 Mori .................. 364/414
4,789,929 12/1988 Nishimura et al. .
5,218,623 6/1993 Tobi et al. ............... 378/15

FOREIGN PATENT DOCUMENTS

0024028A1 2/1981 European Pat. Off. .
0383232A2 8/1990 European Pat. Off. .
4103588 5/1992 Germany .

OTHER PUBLICATIONS

U. Hiroyuki, Patent Abstracts of Japan, vol. 14, No. 484, JP2196383, Oct. 22, 1990.

*Primary Examiner*—Craig E. Church
*Attorney, Agent, or Firm*—Finnegan, Henderson, Farabow, Garrett & Dunner

[57] ABSTRACT

In an X-ray CT (computerized tomographic) imaging method, scano data is produced from X-ray projection image data about a helically-scanned biological body under medical examination. The X-ray projection image data are acquired only at a predetermined projection angle such as 0° during a helical scanning operation. Accordingly, no X-ray projection to acquire the scano data is required to reduce X-ray dose given to the biological body. The X-ray CT imaging method comprises the steps of: scanning a biological body under medical examination in a helical scanning mode, while relatively rotating an X-ray tube and an X-ray detector around the biological body translated along a longitudinal axis of the biological body, to acquire X-ray projection image data about the helically-scanned biological body; selecting only X-ray projection image data acquired at a predetermined projection angle from the entire X-ray projection image data obtained at the helical-scanning step; processing said selected X-ray projection image data to produce a scanogram of said helically-scanned biological body; and reconstructing an X-ray CT image of said helically-scanned biological body based upon said entire X-ray projection image data, whereby both of said scanogram and said X-ray CT image are substantially simultaneously displayed.

26 Claims, 14 Drawing Sheets

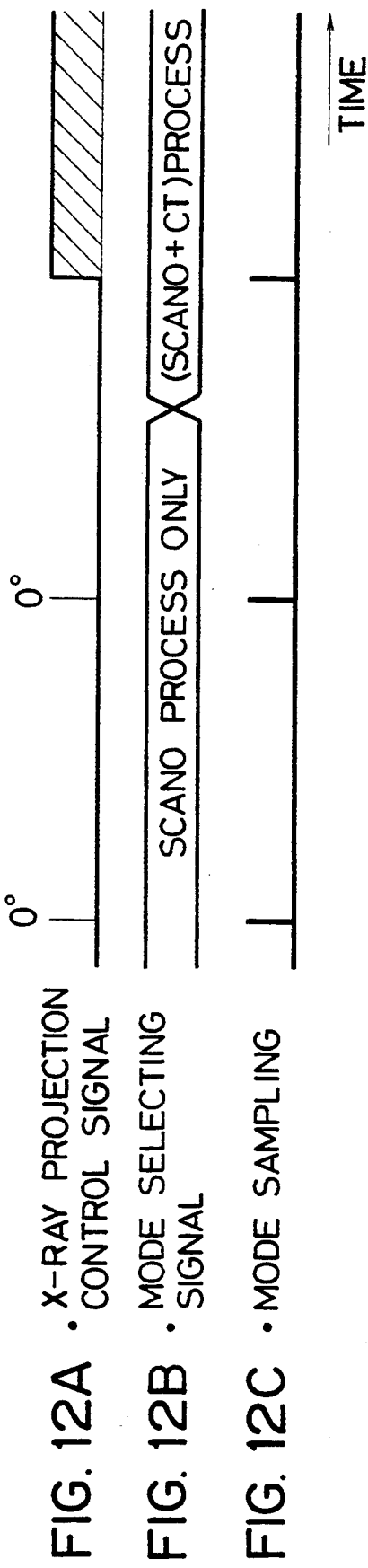
FIG. 12A · X-RAY PROJECTION CONTROL SIGNAL
FIG. 12B · MODE SELECTING SIGNAL
FIG. 12C · MODE SAMPLING
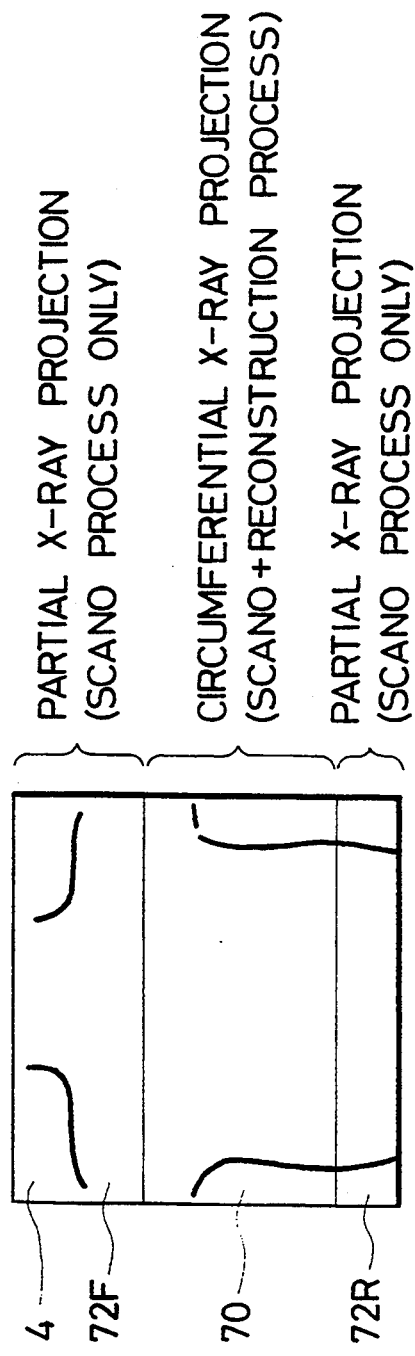
FIG. 14

X-RAY COMPUTERIZED TOMOGRAPHIC IMAGING METHOD AND IMAGING SYSTEM CAPABLE OF FORMING SCANOGRAM DATA FROM HELICALLY SCANNED DATA

BACKGROUND OF THE INVENTION

1. Field of the Invention

The present invention generally relates to an X-ray CT (computerized tomographic) imaging method and an X-ray CT imaging system. More specifically, the present invention is directed to an X-ray CT imaging method and an imaging system capable of producing scano data from X-ray projection image data of a biological body acquired by helically scanning this biological body.

2. Description of the Prior Art

Generally speaking, to image a biological body under medical examination by utilizing a conventional X-ray CT system, a scano image (scanogram) of this biological body is first obtained by projecting X-ray beams to the overall portion of the biological body, with maintaining the X-ray source and detector at a fixed position. Based upon the scano image, positioning operation of tomographic images is carried out to determine a desired diagnostic portion of the biological body. Thereafter, while the X-ray source is rotated together with the X-ray detector around the diagnostic portion, this diagnostic portion of the biological body is scanned by way of the X-ray pulses to acquire X-ray projection image data, and then, the X-ray projection image data are processed to finally obtain X-ray CT image data. When such a scanogram is produced, while a couch on which the biological body is mounted is translated along a longitudinal direction of this biological body, the normal X-ray projection is performed without rotating the X-ray source around the biological body (namely, with fixing the X-ray source). Accordingly, the X-ray projection data are obtained and processed to form a scanogram 30 as represented in FIG. 1.

Subsequently, in the conventional X-ray CT imaging system, positioning of the CT images is performed with respect to this scanogram 30 at doted positions $L_1$, $L_2$, ... $L_n$ ("n" being an integer) as shown In FIG. 1. Then, the couch on which the biological body under medical examination is once returned to the home position, and thereafter, is again translated to position the first CT imaging position "$L_1$" just under the X-ray source (not shown) and the X-ray detector (not shown either), which are rotated during the X-ray scanning operation. As a result, a series of X-ray projection data are acquired after the CT imaging operation at the final CT imaging position "$L_n$" is accomplished.

As previously described, the conventional X-ray CT imaging system necessarily requires a lengthy examination time duration until the desirable CT images are obtained, since first the biological body is translated so as to obtain the scanogram 30, secondly this biological body is returned to the home position, and thirdly the biological body is again translated in order to obtain the X-ray CT image data. In other words, the biological body under medical examination such as a patient must endure such a lengthy and afflictive medical examination. Moreover, there are some risks that the relative position between the X-ray source and the patient differs from each other during the scanogram data acquisition and the CT image data acquisition. Even if, for instance, the first CT imaging position "$L_1$" is accurately determined on the scanogram 30, an actual CT imaging position on the patient may be positionally shifted.

SUMMARY OF THE INVENTION

The present invention has been made in an attempt to solve the above-described problems of the conventional X-ray CT imaging system, and therefore, has an object to provide such X-ray CT imaging method/system capable of producing a scanogram within a short examination time.

Another object of the present invention is to provide X-ray CT imaging method/system capable of obtaining a scanogram at high positional precision with respect to CT images of a biological body under medical examination.

To achieve the above-described objects, an X-ray CT (computerized tomographic) imaging method, according to the present invention, comprises the steps of:

scanning a biological body (20) under medical examination in a helical scanning mode, while relatively rotating an X-ray tube (10) and an X-ray detector (12) around the biological body (20) translated along a longitudinal axis of the biological body (20), to acquire X-ray projection image data about the helically-scanned biological body (20);

selecting only X-ray projection image data acquired at a predetermined projection angle from the entire X-ray projection image data obtained at the helical-scanning step;

processing said selected X-ray projection image data to produce a scanogram (22) of said helically-scanned biological body (20); and reconstructing an X-ray CT image (21) of said helically-scanned biological body (20) based upon said entire X-ray projection image data, whereby both of said scanogram (22) and said X-ray CT image (21) are substantially simultaneously displayed.

Further, another X-ray CT imaging method of the present invention comprises the steps of:

scanning a biological body (20) under medical examination in a helical scanning mode, while relatively rotating an X-ray tube (10) and an X-ray detector (12) around the biological body (20) translated along a longitudinal axis of the biological body (20), to acquire X-ray projection image data about the helically-scanned biological body (20);

selecting only X-ray projection image data acquired at first and second projection angles from the entire X-ray projection image data obtained at the helical-scanning step;

processing said selected X-ray projection image data to produce first and second scanograms (26:27) of said helically-scanned biological body (20); and reconstructing an X-ray CT image (21) of said helically-scanned biological body (20) based upon said entire X-ray projection image data, whereby both of said first and second scanograms (26:27) and said X-ray CT image (21) are substantially simultaneously displayed.

Moreover, in accordance with the present invention, an X-ray CT (computerized tomographic) imaging method comprises the steps of:

scanning a first portion of a biological body (20) under medical examination in a helical scanning mode, while relatively rotating an X-ray tube (10) and an X-ray detector (12) around the biological body (20) translated along a longitudinal axis of the biological body (20), to acquire first X-ray projection image data about the helically-scanned first portion of the biological body (20);

partially scanning a second portion of said biological body (20) under medical examination by intermittently projecting an X-ray beam to the second portion of the biological body (20) from the X-ray tube (10), to acquire second X-ray projection image data about the partially-scanned second portion of the biological body (20);

processing said second X-ray projection image data to produce a scanogram (22) of said partially-scanned second portion of the biological body (20); and reconstructing an X-ray CT image (21) of said helically-scanned biological body (20) based upon said first X-ray projection image data, whereby both of said scanogram (22) and said X-ray CT image (21) are substantially simultaneously displayed.

In addition, according to the present invention, an X-ray CT (computerized tomographic) imaging system (100:400) comprising:

scanning means (2) including an X-ray tube (10) and an X-ray detector (12), for scanning a biological body (20) under medical examination in a helical scanning mode, while relatively rotating said X-ray tube (10) and said X-ray detector (12) around the biological body (20) translated along a longitudinal axis of the biological body (20), to acquire X-ray projection image data about the helically-scanned biological body (20);

scano data processing means (8:90) for selecting only X-ray projection image data acquired at a predetermined projection angle from the entire X-ray projection image data, and for processing said selected X-ray projection image data to produce a scanogram (22) of said helically-scanned biological body (20);

CT image reconstructing means (7) for reconstructing an X-ray CT image (21) of said helically-scanned biological body (20) based upon said entire X-ray projection image data; and display means (4) for substantially simultaneously displaying both of said scanogram (22) and said X-ray CT an image (21).

BRIEF DESCRIPTION OF THE DRAWINGS

For a better understanding of the present invention, reference is made of the following specification in conjunction with the accompanying drawings, in which:

FIG. 12A to 12C show operation timing charts of the third X-ray CT imaging system 300;

FIG. 14 schematically represents the partial X-ray projection mode and the circumferential X-ray projection mode effected in the third X-ray CT imaging system 300;

DETAILED DESCRIPTION OF THE PREFERRED EMBODIMENTS

ARRANGEMENT OF FIRST X-RAY CT IMAGING SYSTEM

Figure 1:
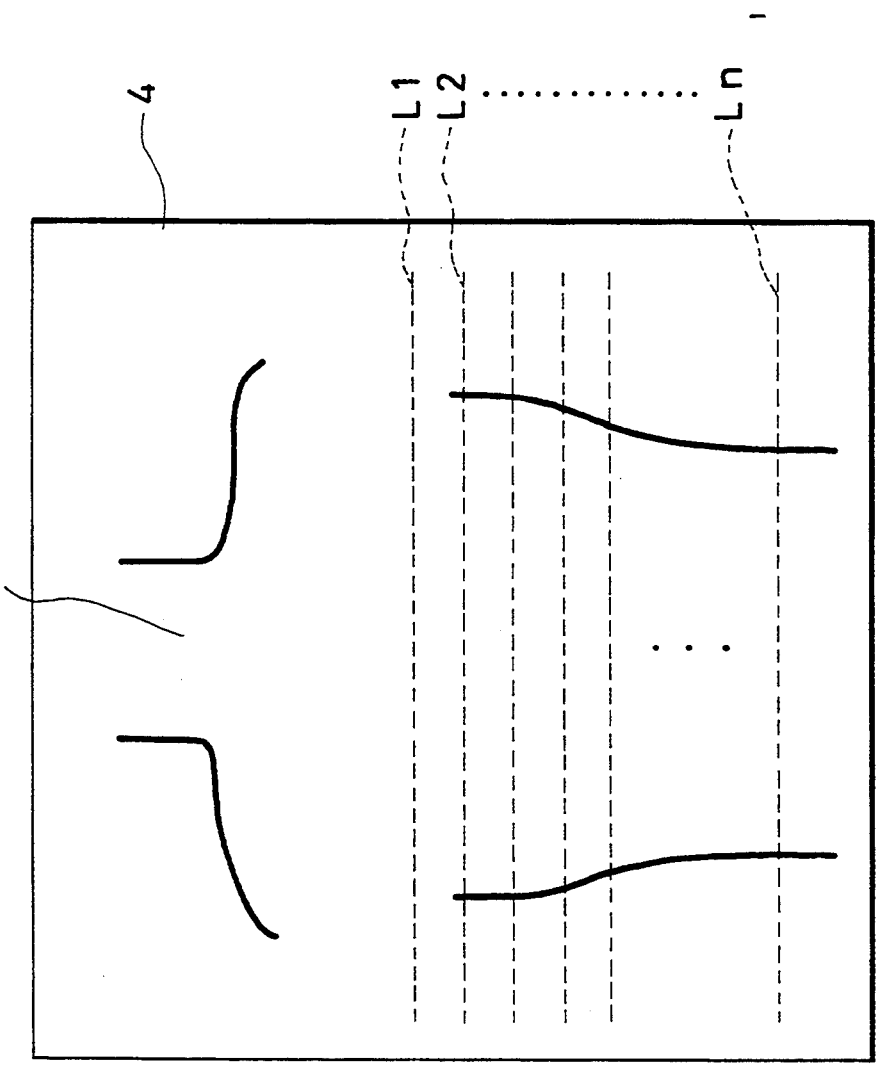
FIG. 1 schematically illustrates a scanogram 30 produced in the conventional X-ray CT imaging method.
Figure 2:
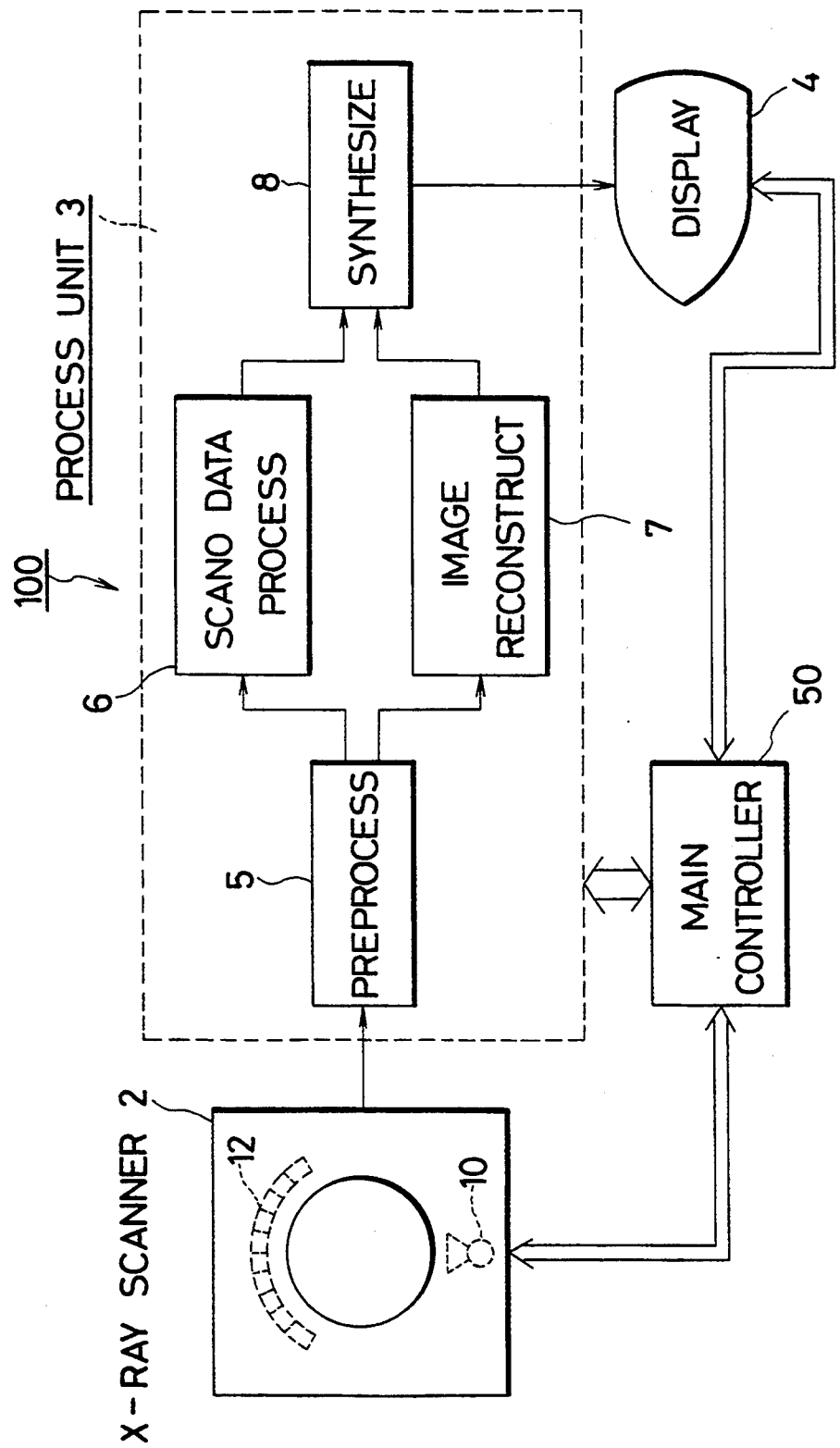
FIG. 2 is a schematic block diagram for showing an arrangement of an X-ray CT imaging system 100 according to a first preferred embodiment of the present invention.

In FIG. 2, there is shown an arrangement of an X-ray CT (computerized tomographic) imaging system 100 according to a first preferred embodiment of the present invention.

The first X-ray CT imaging system 100 is mainly constructed of an X-ray scanner 2 for performing X-ray scanning operation with respect to a biological body under medical examination such as a patient 20 (shown in FIG. 3) to produce X-ray projection data; a data processing unit 3 for processing the X-ray projection data; a display unit 4 for displaying both of a scanogram and an X-ray CT image; and a main controller 50. The data processing unit 3 includes a preprocessing unit 5 for preprocessing the X-ray projection data derived from the X-ray scanner 2 to obtain preprocessed X-ray projection data; a scano data processing unit 6 for processing the preprocessed X-ray projection data to produce scano data; an image reconstructing unit 7 for reconstructing a desirable X-ray CT image from the preprocessed X-ray projection data; and a synthesizing unit 8 for synthesizing the above-described scano data and X-ray CT image data in such a manner that both of the scanogram and the CT image of the biological body are displayed on the same screen of the display unit 4 (will be discussed more in detail).

OPERATION OF FIRST X-RAY CT IMAGING SYSTEM

It should be understood that according to the present invention, the patient 20 is helically scanned only one time by the X-ray scanner 2 of the first X-ray CT imaging system 100 so as to obtain both of scano data and CT image data. That is to say, since the X-ray projection data are acquired during only one helical scanning operation and thereafter both of the scano data and the CT image data are produced from this series of X-ray projection data, the couch (not shown in detail) on which the patient 20 is laid is translated only one time along a longitudinal direction thereof.

Figure 3:
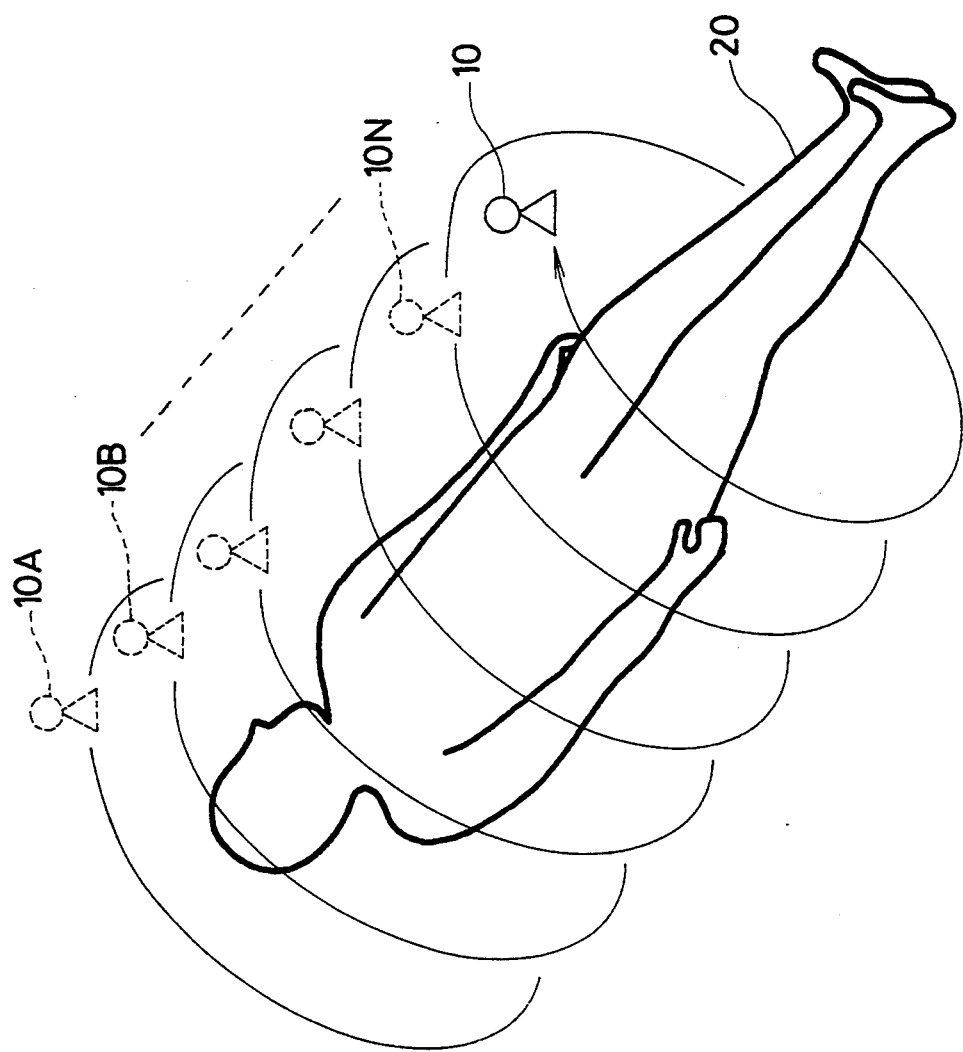
FIG. 3 schematically illustrates the helical scanning operation and the X-ray projection positions to obtain a scanogram by the first X-ray CT imaging system 100.

As represented in FIG. 3, the helical scanning operation is performed by the X-ray scanner 2 with respect to the patient 20 in the first X-ray CT imaging system 100 of FIG. 2. For the sake of simplicity, although an X-ray detector unit 12 is positioned opposite to an X-ray tube 10, this detector unit 12 is omitted from FIG. 3. The X-ray helical scanning operation per se is known from, for instance, U.S. Pat. No. 4,630,202 issued to Mori, entitled "COMPUTERIZED TOMOGRAPHIC APPARATUS UTILIZING A RADIATION SOURCE", patented on Dec. 16, 1986. Roughly speaking, while the X-ray tube 10 employed in the X-ray scanner 2 is rotated around the patient 20, the patient 20 (couch) is translated along a longitudinal direction of the patient 20, so that the relative trail of the X-ray tube 10 with respect to the patient 20 represents a helical shape (see FIG. 3). Predetermined (same phase) positions are indicated by reference numerals 10A, 10B, ... 10N, which imply, for instance, 0°, 360°, ... 360°×N ("N" being an integer).

Referring now to the arrangement of the first X-ray CT imaging system 100 shown in FIG. 2 and an operation flow of this imaging system 100 shown in FIG. 4, acquisition of the scano data about the patient 20 from the helically-scanned X-ray projection data will be described.

Figure 4:
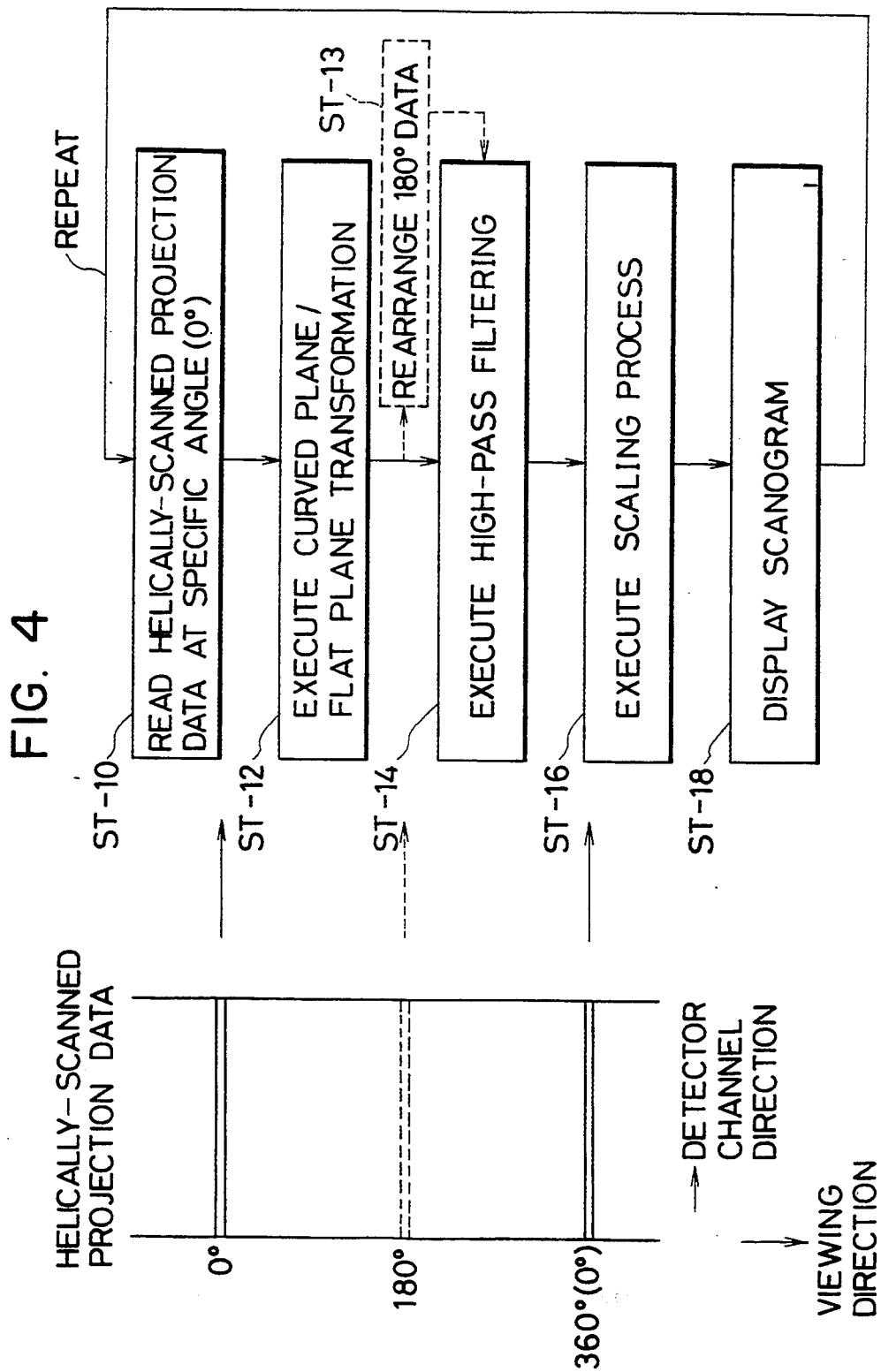
FIG. 4 is a flow chart for explaining the scano data/CT image reconstruction process operation performed by the first X-ray CT imaging system 100.

As shown in a lefthand portion of this operation flow in FIG. 4, a series of X-ray projection data obtained by helically scanning the patient 20 is continuously acquired from the X-ray scanner 2 under control of the main controller 50.

Figure 6:
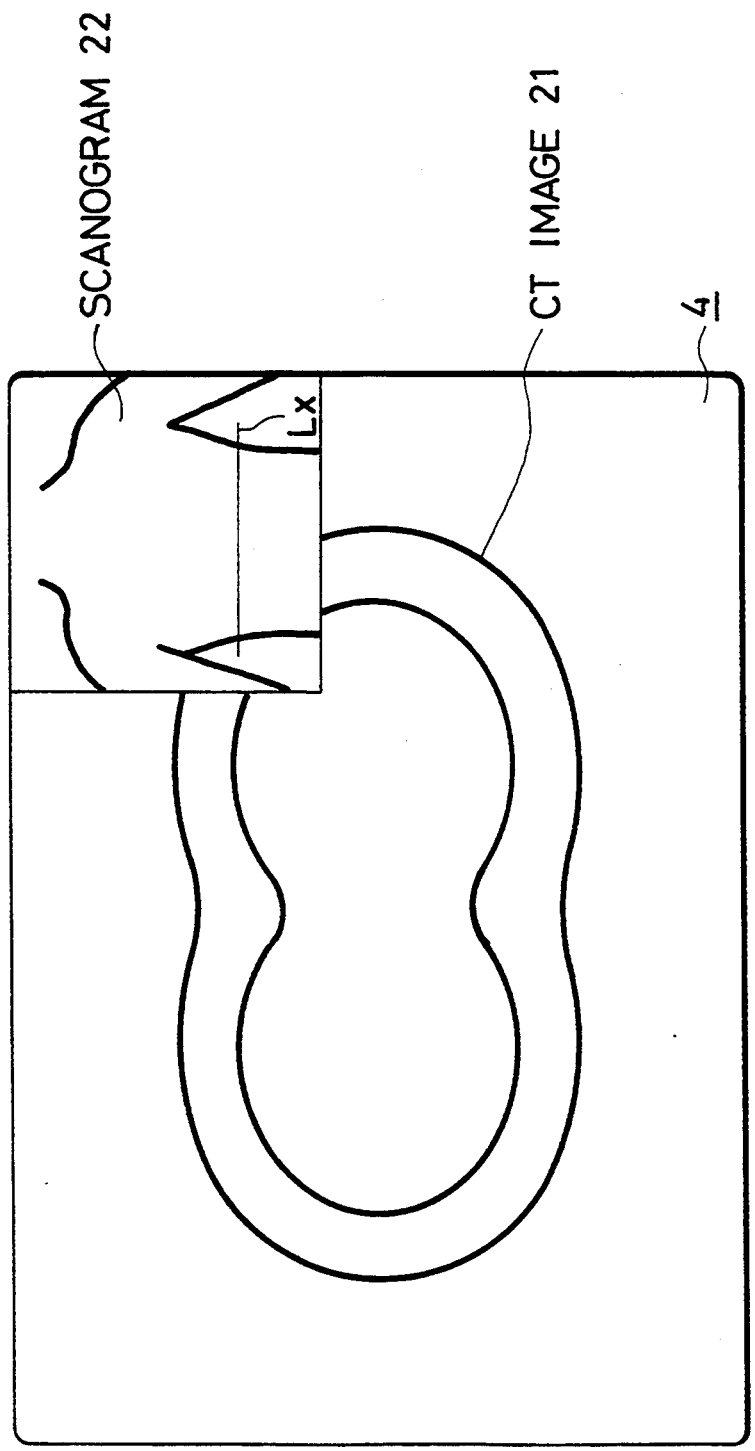
FIG. 6 is a display screen for displaying both a scanogram 22 and a CT image 23 in the first X-ray CT imaging system 100.

In a flow chart indicated in a righthand portion of FIG. 4, only the helically-scanned projection data acquired at a preselected projection angle, for instance, 0° or 360° (corresponding to the positions 10A, 10B, ... 10N) are read out from the above-described series of helically-scanned X-ray projection data at a first step ST-10. At the next step ST-12, the read projection data acquired at the specific projection angle of 0° (360°) are processed by a curved plane/flat plane transformation, since the X-ray detector unit 12 (see FIG. 2) is constructed of a plurality of detector channels having curved surfaces. Then, the plane-transformed projection data are further processed in a high-pass filter (not shown in detail) at a step ST-14. Subsequently, the filtered projection data are processed by a scaling process at a step ST-16. Finally, the scaling-processed projection data (corresponding to the scano data) are displayed as a scanogram 22 (see FIG. 6) on the display unit 4 at a step ST-18. Then, this flow operation is repeated from the previous step ST-10.

As a consequence, the scanogram 22 of the patient 20 can be obtained by processing only the helically-scanned X-ray projection data acquired at the specific projection angle (0°) in the scano data processing unit 6 under control of the main controller 50.

On the other hand, if helically-scanned X-ray projection data acquired at another specific projection angle "180°" indicated by a dot line of FIG. 4 are also processed to obtain such a scano data, the following additional process step is required in the process flow shown in FIG. 4. That is, after the helically-scanned projection data acquired at two specific projection angles of 0° and 180° are read out at the step ST-10 and processed by the curved plane/plane transformation at the step ST-12, only the processed projection data acquired at the specific projection angle 180° are rearranged at a step ST-13. This is because the positional relationship of the detector channel is completely opposite to each other with respect to the projection angles 0° and 180°.

Figure 5:
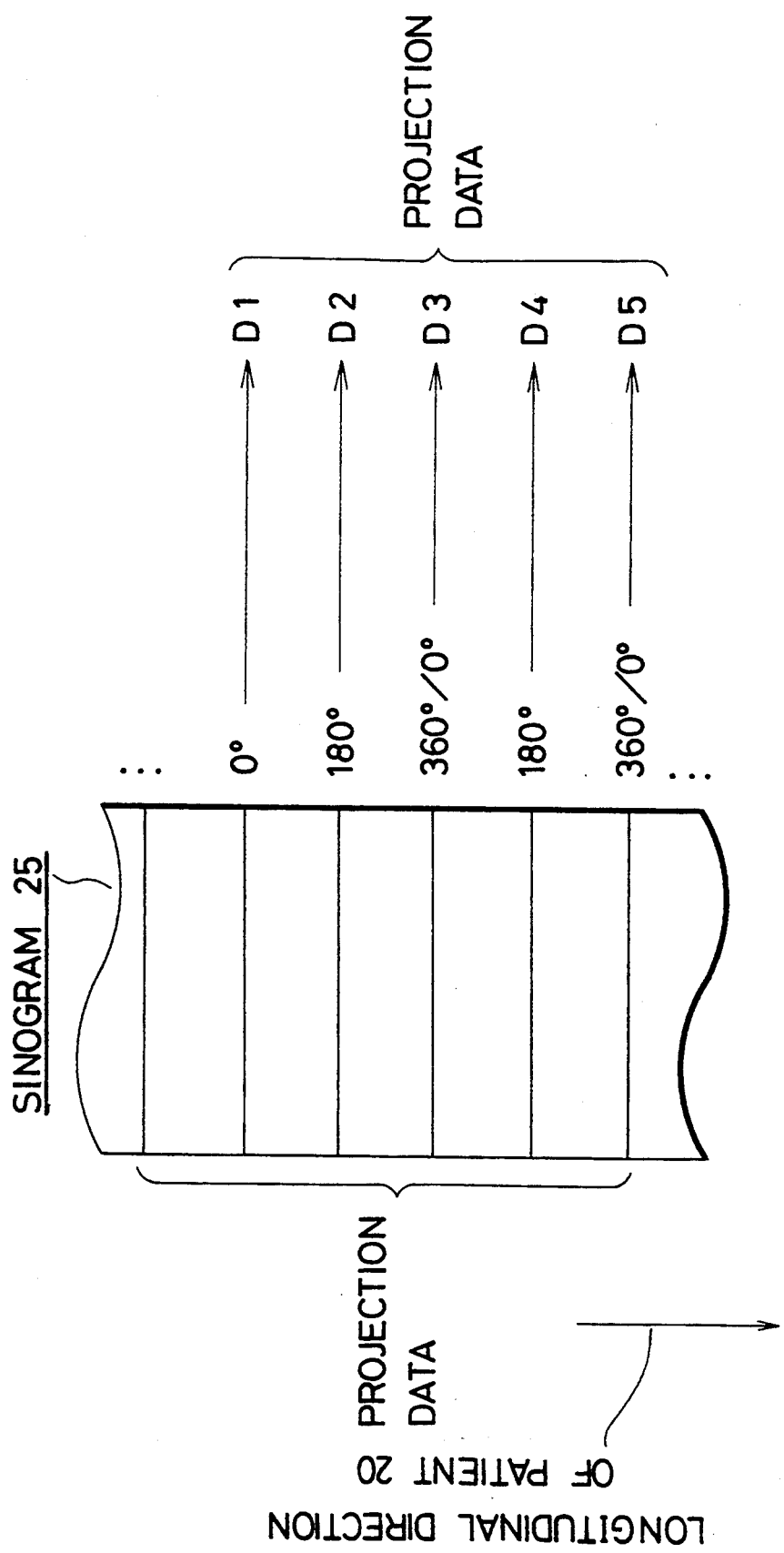
FIG. 5 schematically illustrates a sinogram 25 of the first X-ray CT imaging system 100.

The above-described scanogram formation will now be pictorially explained with reference to FIG. 5. FIG. 5 represents a so-called "sinogram" 25 constructed of a plurality of projection data "D1", "D2", ... "DS". A desirable scanogram 22 is obtained by arranging these projection data "D1 (angle of 0°)", "D2 (angle of 180°)", "D5 (angle of 360°)" along the longitudinal direction of the patient 20. As previously described, it should be noted that since the arrangement of the projection data D1, D3, D5 acquired at the angle of 0° along the detector's channel direction is completely reversed with respect to that of the projection data D2, D4 acquired at the angle of 180°, either projection data should be rearranged in order to obtain the desirable scanogram 22.

Referring back to FIG. 2, the above-described series of helically-scanned X-ray projection data are preprocessed in the preprocessing unit 5, and thereafter are reconstructed in the image reconstructing unit 7 so as to produce desirable CT image data under control of the main controller. Both of this desirable CT image data and the above-mentioned scano data are synthesized in the synthesizing unit 8, so that both of a desirable CT image 21 and a desirable scanogram 22 are simultaneously displayed on the same screen of the display unit 4. In this scanogram 22, a line "$L_x$" indicates a position on the patient 20, where this CT image 21 has been obtained.

In accordance with the first X-ray CT imaging system 100, since both of the scanogram 22 and the CT image 23 can be obtained at the same time by performing only a single helical scanning operation with respect to the patient 20, the entire medical examination time during which the patient 20 must endure can be considerably reduced, as compared with that of the conventional X-ray CT imaging system. Accordingly, since such a lengthy and afflictive medical examination can be mitigated, this X-ray CT imaging system 100 is suitable for a so-called "group diagnosis" in which X-ray imaging portions of patients are previuosly determined and a large number of medical examination processes must be carried out within a limited time period.

Moreover, since the scanogram 22 and the CT image 21 are produced from the same helically-scanned X-ray projection data, there is no positional shift in both of these images. This implies that the positional precision of the CT image can be considerably improved, as compared with that of the conventional CT imaging system.

As apparent from the foregoing descriptions, although the projection angles of the first X-ray CT imaging system 100 are selected to be 0°, 90° and 180°, any other projection angles such as 1°, 150°, 292° may be freely selected to obtain the scanograms.

ARRANGEMENT OF SECOND X-RAY CT IMAGING SYSTEM

Figure 7:
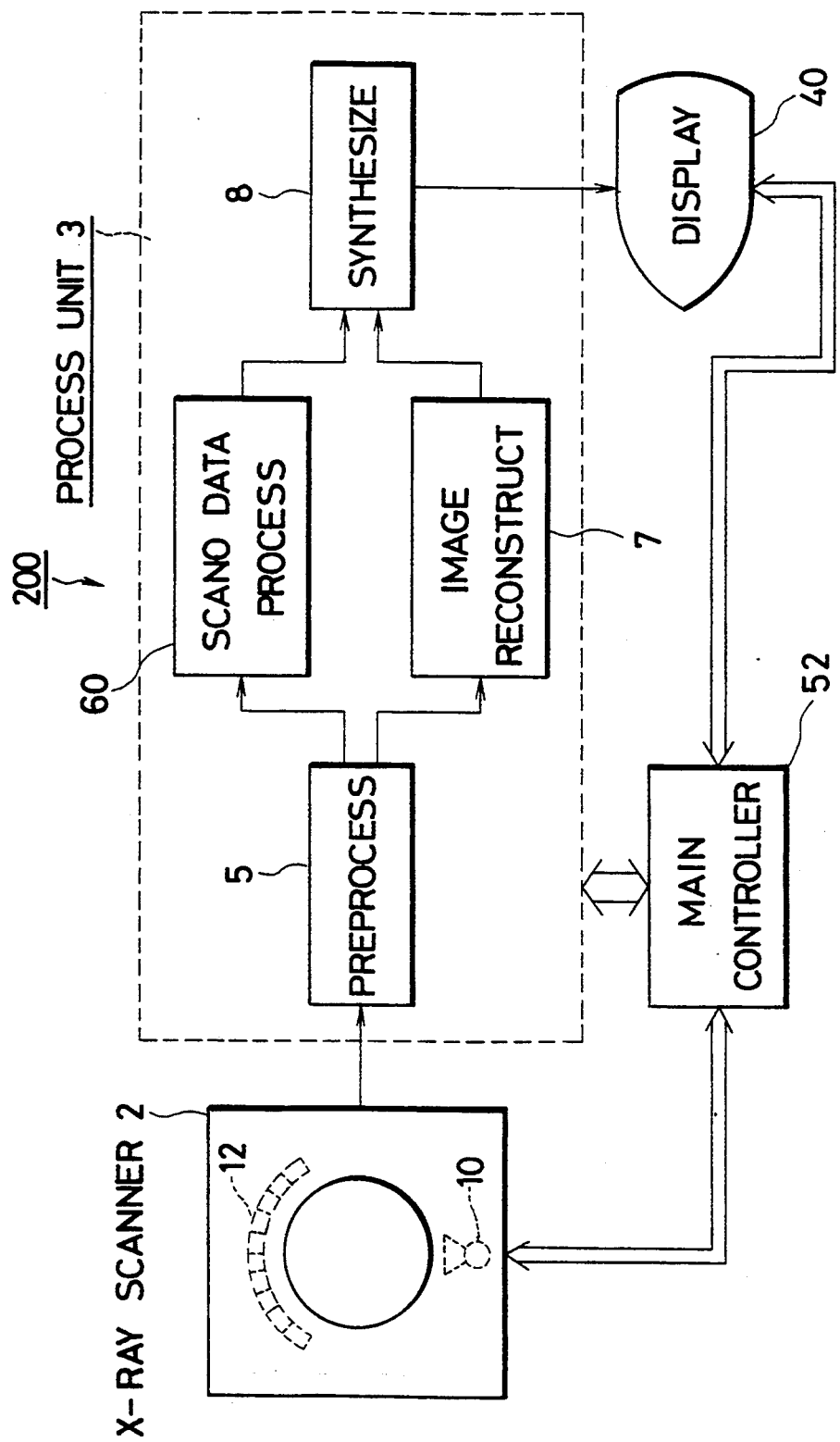
FIG. 7 is a schematic block diagram for representing an arrangement of an X-ray CT imaging system 200 according to a second preferred embodiment of the present invention.
Figure 8:
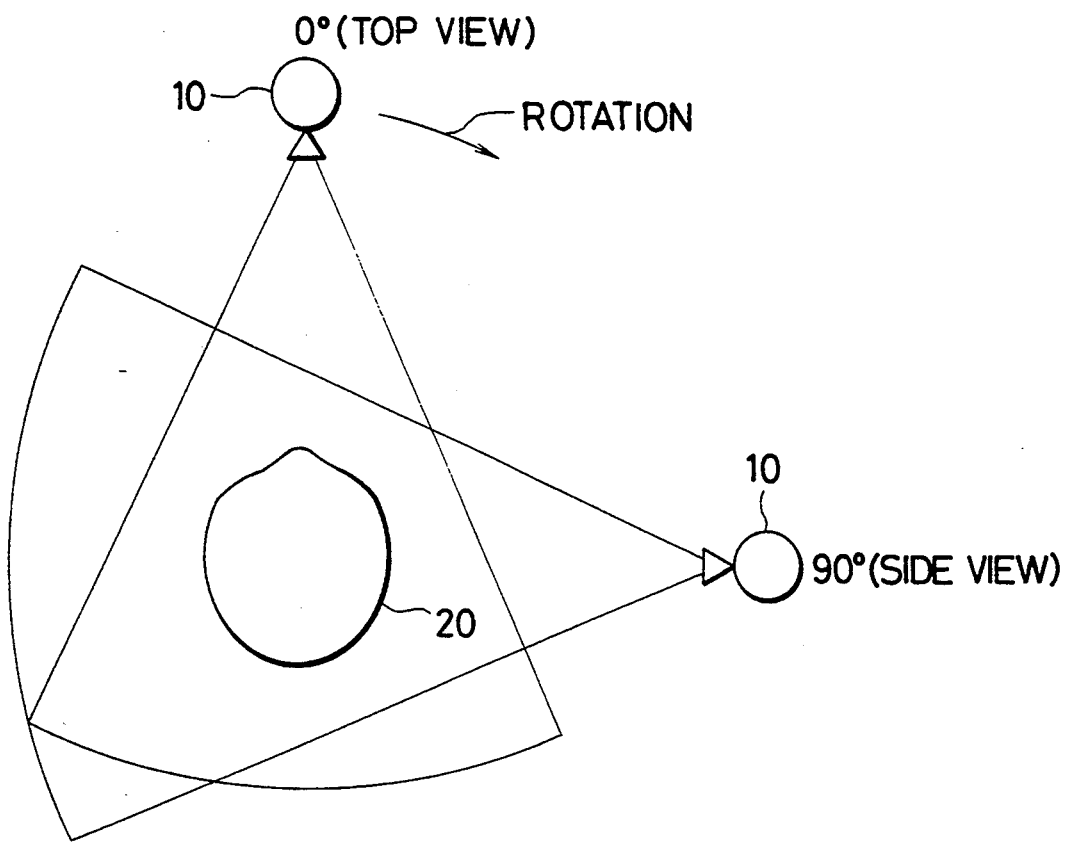
FIG. 8 illustrates how to obtain a top-viewed scanogram and a side-viewed scanogram in the second X-ray CT imaging system 200.

Referring now to FIGS. 7 and 8, an arrangement of an X-ray CT imaging system 200 according to a second preferred embodiment of the present invention will be described.

Figure 10:
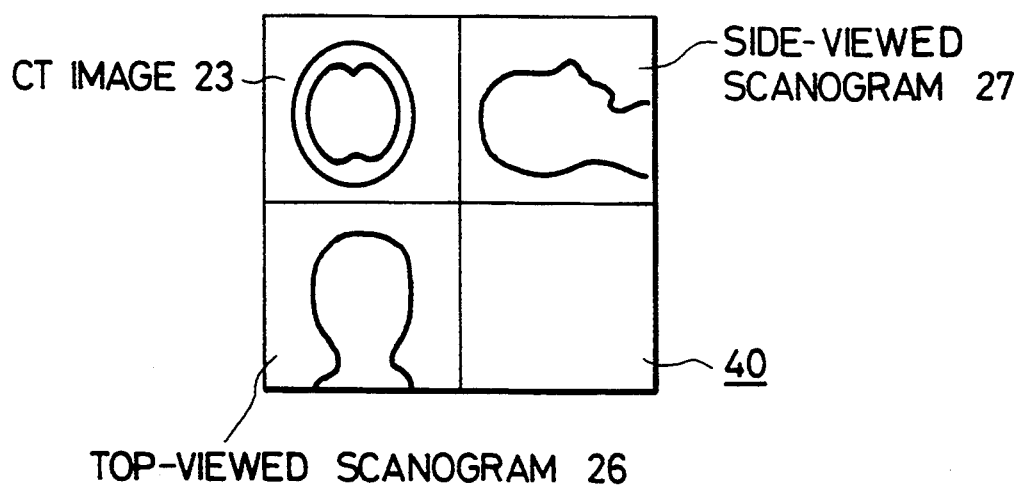
FIG. 10 schematically represents the multiple image display realized in the second X-ray CT imaging system 200.

In the arrangement shown in FIG. 7, a scano data process unit 60 is employed in the process unit 3 and a main controller 52 is employed. Under control of the main controller 52, a series of helically-scanned X-ray projection data are acquired by the X-ray scanner 2 at two specific projection angles of 0° and 90°. Then, one scanogram 26 is obtained as a top view (0°) and the other scanogram 27 is obtained as a side view (90°), as indicated in FIG. 10, which are produced in the scano data process unit 60 under control of the main controller 52.

OPERATION OF SECOND X-RAY CT IMAGING SYSTEM

Referring now to a flow chart of FIG. 9, an overall operation of the second X-ray CT imaging system 200 will be described. Similarly, acquisition timings (projection angles) of the helically-scanned X-ray projection data and projection data process operations are represented at a lefthand portion of FIG. 9, whereas an operation flow of the second CT imaging system 200 is indicated at a righthand portion of FIG. 9.

Figure 9:
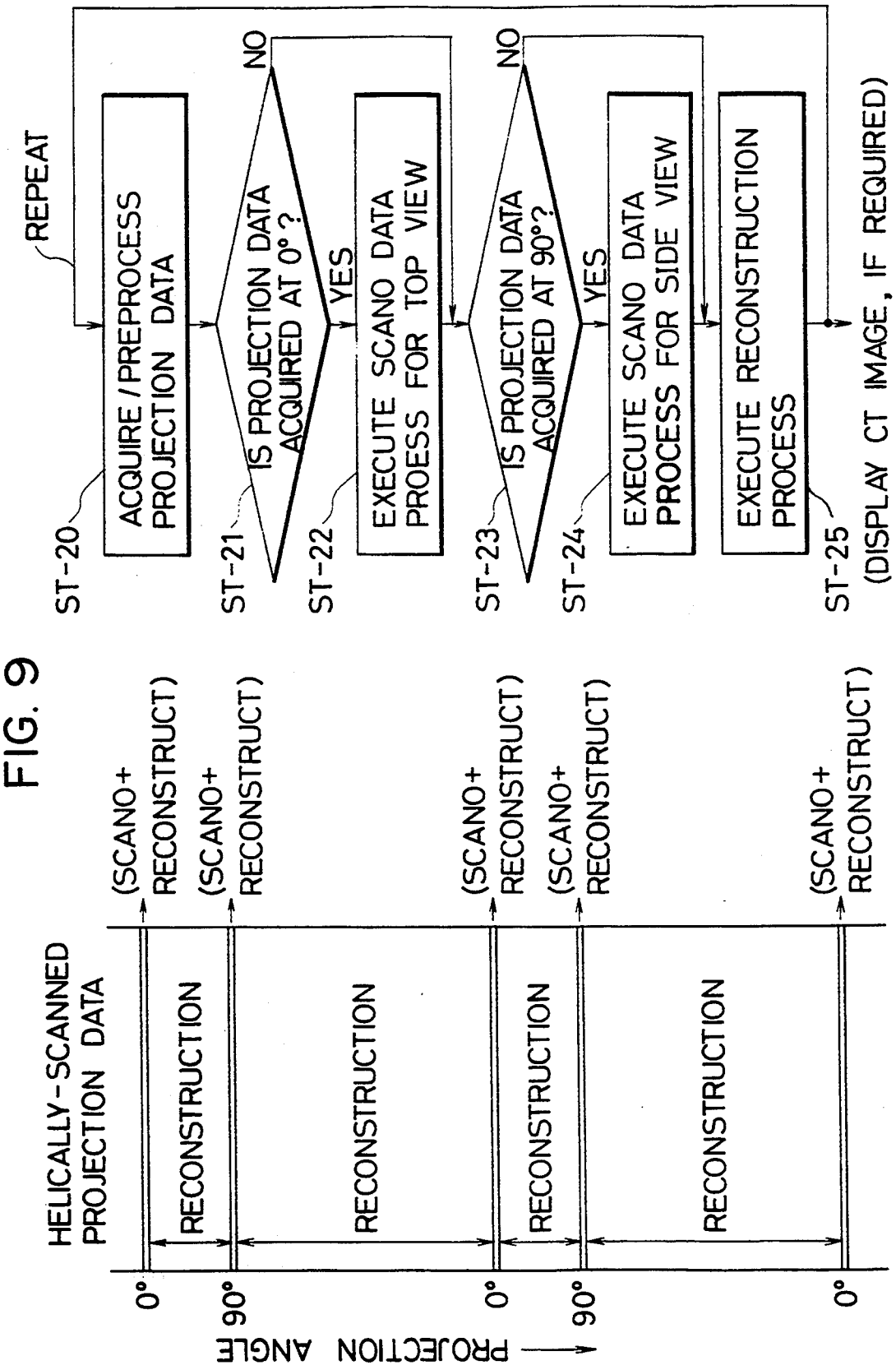
FIG. 9 is a flow chart for explaining the scano data/CT image reconstruction process operation executed by the second X-ray CT imaging system 200.

As apparent from the lefthand portion of FIG. 9, both of the scanogram production and the CT image reconstruction are simultaneously performed at the respective specific projection angles of 0° and 90°, whereas only the CT image reconstruction is carried out at any projection angles other than the specific projection angles.

At a first step ST-20, a series of helically-scanned X-ray projection data are acquired by the X-ray scanner 2 under control of the main controller 52, and then are preprocessed in the preprocess unit 5 under control of the main controller 52. At the subsequent step ST-21, a check is made as to whether or not the helically-scanned projection data has been acquired at the first specific projection angle of 0°. If YES, then the process operation is advanced to a step ST-22 at which the scano data process for the top view 26 (see FIG. 10) is performed in the scano data process unit 60 with respect to the helically-scanned projection data acquired at the angle of 0°.

To the contrary, if the helically-scanned projection data does not correspond to the projection data acquired at the first specific projection angle of 0° at the previous step ST-21, then the process operation is Jumped to a further step ST-23. At this step ST-23, another check is made as to whether or not this helically-scanned projection data has been acquired at the second specific projection angle of 90°. If YES, then the process operation is advanced to the next step ST-24 at which the scano data process for the side view 27 (see FIG. 10) is executed in the scano data process unit 60 under control of the main controller 52.

Conversely, if the helically-scanned projection data has not been acquired at the second specific projection angle of 90° at the previous step ST-23, then the process operation is Jumped to a further step ST-25. At this step ST-25, the CT image reconstruction process is carried out with respect to the projection data in the image reconstruction unit 7 under control of the main controller 52. Thereafter, the above-described process operation is repeated from the first step ST-20. The resultant CT image 23 produced at the step ST-25 may be displayed in combination with both of the top-viewed scanogram 26 and the side-viewed scanogram 27, as represented in FIG. 10, if required.

It should be noted that all of the helically-scanned X-ray projection data acquired at both of the first and second specific projection angles of 0° and 90°, are similarly processed in the image reconstruction unit 7 to obtain CT images acquired at these specific projection angles.

In accordance with the above-described second X-ray CT imaging system 200, since both of the top-viewed scanogram 26 and the side-viewed scanogram 27 can be obtained at the same time, such a multiple image display can be realized in, for instance, a 1024-metrix display unit 40, as represented in FIG. 10.

ARRANGEMENT OF THIRD X-RAY CT IMAGING SYSTEM

Figure 11:
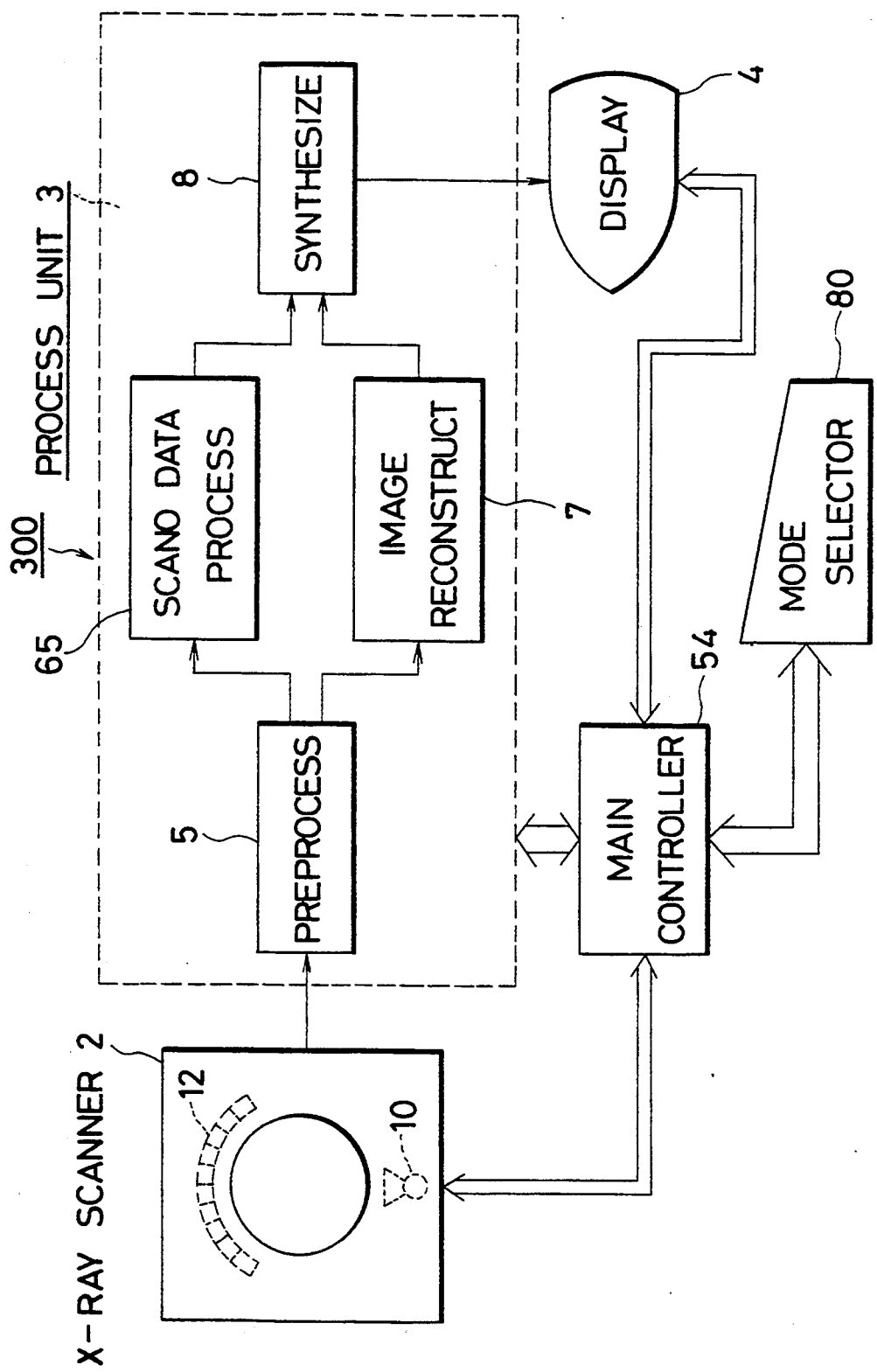
FIG. 11 is a schematic block diagram for representing an arrangement of an X-ray CT imaging system 300 according to a third preferred embodiment of the present invention.

In FIG. 11, there is shown an arrangement of an X-ray CT imaging system 300 according to a third preferred embodiment of the present invention.

A major feature of this third X-ray CT imaging system 300 is such that a scano data process unit 65 is employed in the process unit 3 and is operated in conjunction with a mode selector 80 under control of a main controller 54 to select the operation mode of the third X-ray CT imaging system 300. That is, a selection is made between only scano data process, and also a combination of the scano data process with the CT image reconstruction process via the mode selector 80 by an operator. As shown in FIGS. 12A to 12C, the mode selector 80 issues a mode selecting signal of FIG. 12B to the main controller 54. Then, if only the scano data process (scanogram formation) is selected, an X-ray projection control signal shown in FIG. 12A is produced from the main controller 54 only at a preselected projection angle, e.g., 0°. Accordingly, the X-ray tube 10 of FIG. 11 is energized In response to this X-ray projection control signal, so that X-ray beams are projected therefrom only at the preselected projection angle of 0°. Thus, there is a merit that the patient 20 receives only a limited quantity of X-ray dose during this operation mode. In other words, although both of the X-ray tube 10 and the X-ray detector unit 12 are helically scanned around the patient 20, the X-ray beams are intermittently projected from the X-ray tube 10 during the helical scanning operation at the preselected projection angle, which does not correspond to the normal helical scanning operation (will be referred to a "partial X-ray projection").

To the contrary, if the operator selects the combination process (namely, the scano data process and the CT image reconstruction process) by the mode selector 80, another mode selecting signal is issued from the main controller 54. Then, the above-described normal helical scanning operation is carried out (will be referred to a "circumferential X-ray projection"), so that while the scanogram data is produced in the scano data process unit 65, the X-ray CT image is reconstructed in the image reconstruction unit 7.

OPERATION OF THIRD X-RAY CT IMAGING SYSTEM

Figure 13:
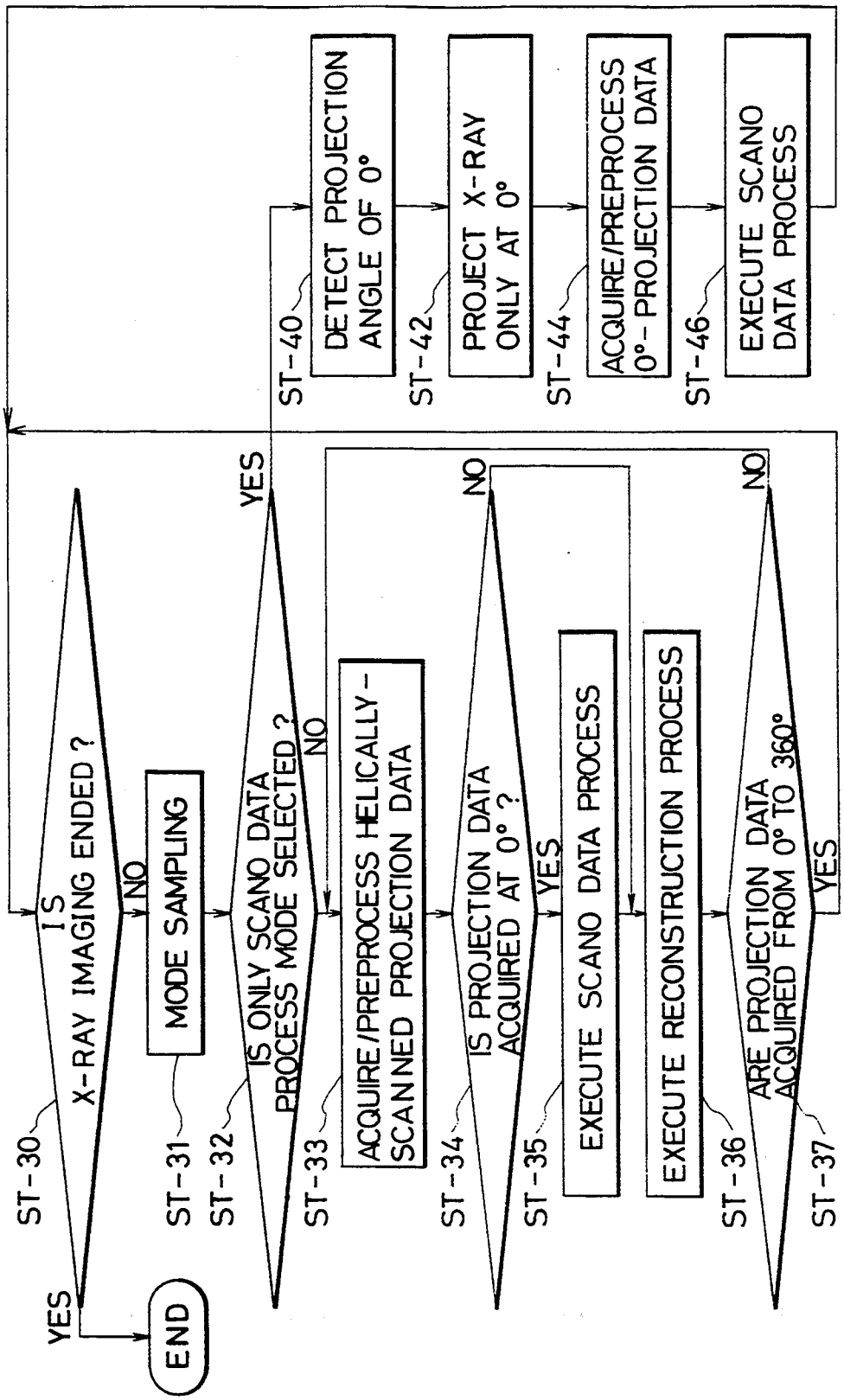
FIG. 13 is a flow chart for explaining the entire process operation of the third X-ray CT imaging system 300.

FIG. 13 represents a flow chart of overall operation by the third X-ray CT imaging system 300 of FIG. 11.

At a first step ST-30, a check is done as to whether or not the X-ray imaging operation is completed. If NO, then the process operation is advanced to the next step ST-31 at which mode sampling is performed. Then, another check is made as to whether or not only the scano data process is selected. If NO, then the process operation is advanced to the subsequent step ST-33. At this step ST-33, since the combination process of the scano data and the CT image reconstruction is selected by the operator via the mode selector 80, the above-described normal helically-scanned X-ray projection data are acquired by the X-ray scanner 2 and thereafter preprocessed in the preprocess unit 5 under control of the main controller 54.

Subsequently, another check is made as to whether or not the helically-scanned projection data is acquired at the specific projection angle of 0° at a step ST-34. If YES, then the process operation is advanced to the next step ST-35 at which the scano data process is performed by the scano data process unit 65 under control of the main controller 54. To the contrary, if NO at the previous step ST-34, then the process operation is Jumped to a step ST-36. Then, the X-ray CT image reconstruction process is performed for this helically-scanned projection data in the image reconstruction unit 7 under control of the main controller. After this image reconstruction process has been accomplished at the step ST-36, a further check is made as to whether or not the helically-scanned projection data have been acquired/processed from 0° to 360° (i.e., circumferential X-ray projection process). If NO, then the process operation is returned to the step ST-33, so that a series of projection data process operations is again carried out until the step ST-37. If YES, then the process operation is returned to the first step ST-30, because the combination process operation mode selected by the operator via the mode selector 80 has been completed. Thus, the circumferential X-ray projection (see FIG. 14) is achieved.

On the other hand, if the only scano data process mode is selected (i.e., "YES"), then the process operation is advanced to a new step ST-40. At this step ST-40, a predetermined projection angle, for instance, 0° in the third X-ray CT imaging system 300 is detected under control of the main controller 54. Next, under control of the main controller 54, the X-ray beam is projected from the X-ray tube 10 only at the projection angle of 0° at a step ST-42.

As a result, only 0°-projection data are acquired from the X-ray scanner 2 and then preprocessed by the preprocess unit 5 under control of the main controller 54. Thus, the scano data process operation is executed only for these 0°-projection data in the scano data process unit 65, so that the partial X-ray projection (see FIG. 14) is achieved.

In accordance with the third X-ray CT imaging system 300, there are the following particular advantages. In general, a display region of a scanogram is relatively larger than that of a CT image on a display screen. Furthermore, since an operator observes a CT image with reference to a scanogram, it is suitable for easy observation to display the scanogram with a larger area than that of the CT image on a display screen. To this end, if X-ray beams are projected from the X-ray tube 10 to the patient 20 over the circumferential helical-direction, a total amount of X-ray dose is increased, as compared with that of the partial X-ray projection. Therefore, according to the third X-ray CT imaging system 300, the mode selector 80 manipulated by an operator is newly employed and can select such a partial X-ray projection in conjunction with the main controller 54 to obtain a scanogram under lower X-ray dose. Moreover, when a desirable CT imaging portion 70 of the patient is reached during the helical scanning operation by the X-ray scanner 2 while observing a first scanogram "72F" in real time, an operator manipulates the mode selector 80 to change the partial X-ray projection mode into the circumferential X-ray projection mode. After this circumferential X-ray projection (namely, normal helical scanning operation) has been accomplished for the desirable CT imaging portion 70, the operator again manipulates the mode selector 80 to change the circumferential X-ray projection mode into the partial X-ray projection mode, so that a second scanogram "72R" will be produced. As a consequence, a total amount of X-ray dose given to the patient 20 can be considerably reduced, as compared with in the conventional X-ray CT imaging system.

ARRANGEMENT/OPERATION OF FOURTH X-RAY CT IMAGING SYSTEM

Figure 15:
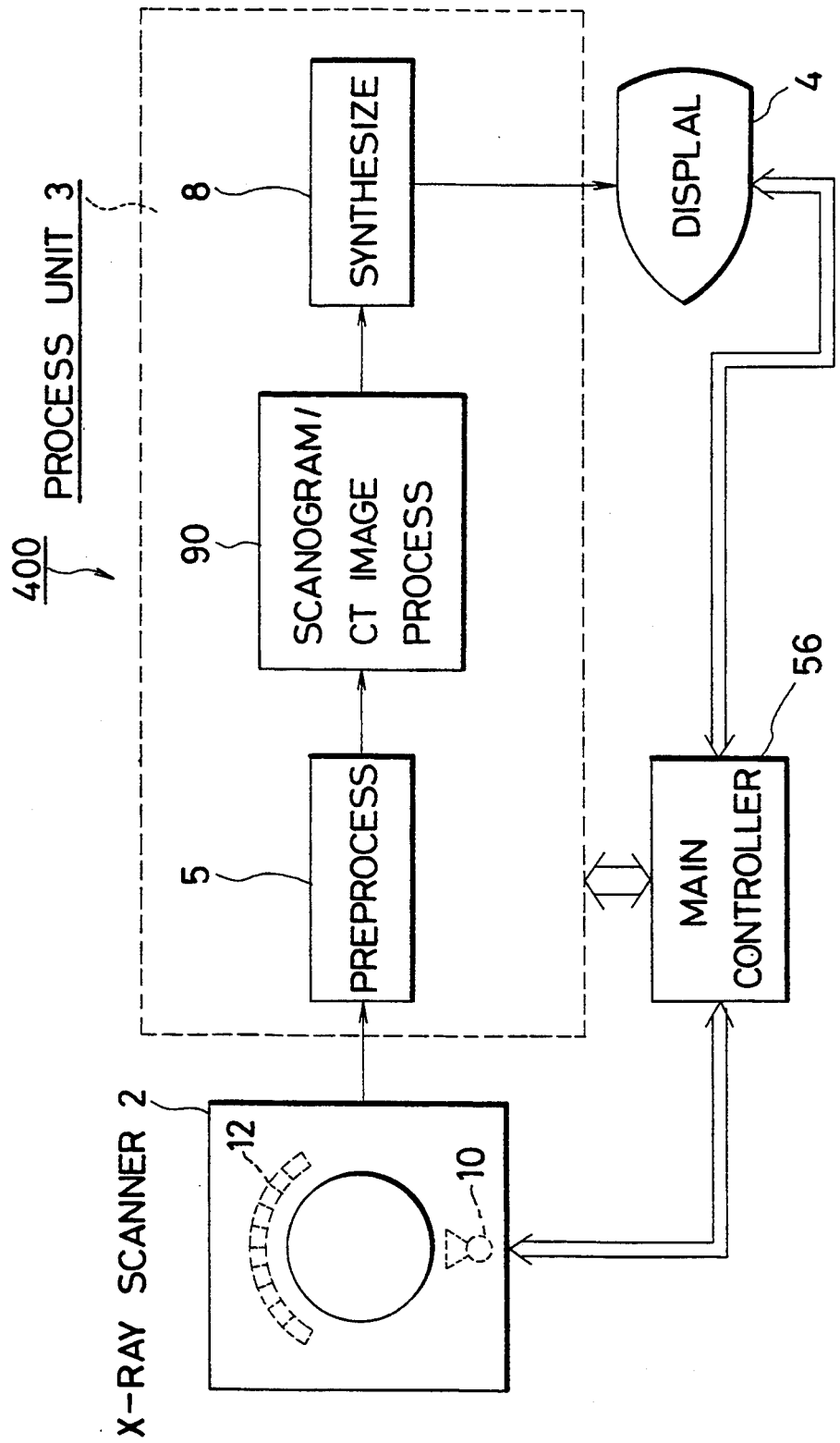
FIG. 15 is a schematic block diagram for representing an arrangement of an X-ray CT imaging system 400 according to a fourth preferred embodiment of the present invention.

FIG. 15 represents an arrangement of an X-ray CT imaging system 400 according to a fourth preferred embodiment of the present invention. A major feature of the fourth X-ray CT imaging system 400 is to employ a scanogram/CT image processing unit 90 in the process unit 3. This scanogram/CT image processing unit 90 is capable of performing a scano data process operation and a CT image reconstruction operation.

Figure 16B:
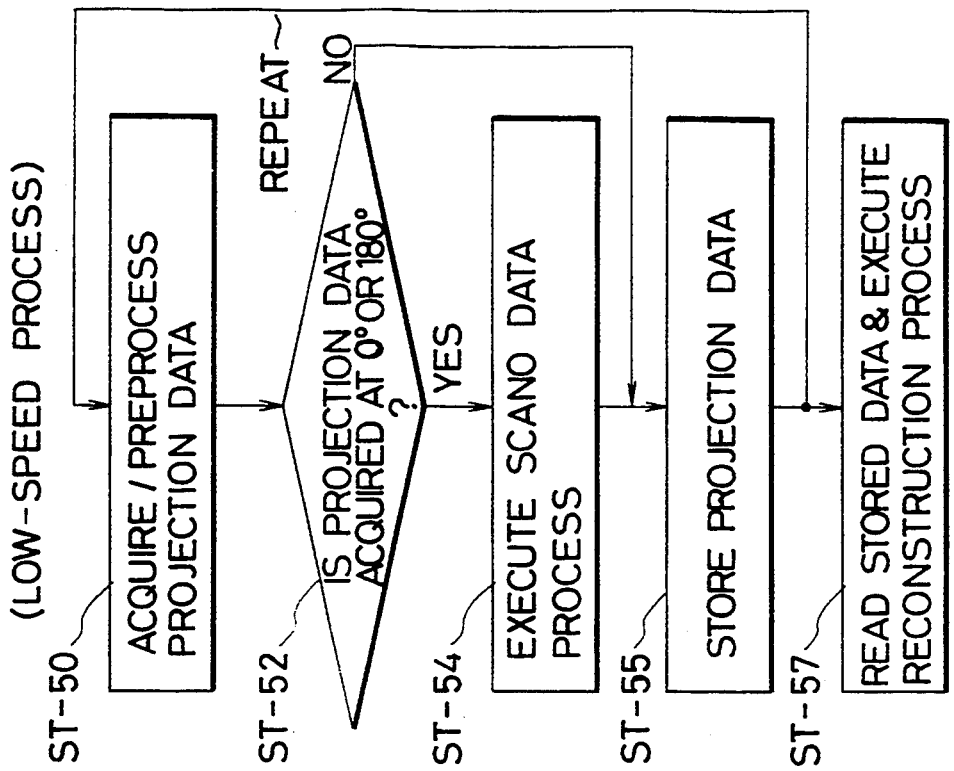
FIG. 16B is a flow chart for explaining the lowspeed process operation by the fourth X-ray CT imaging system 400.
Figure 16A:
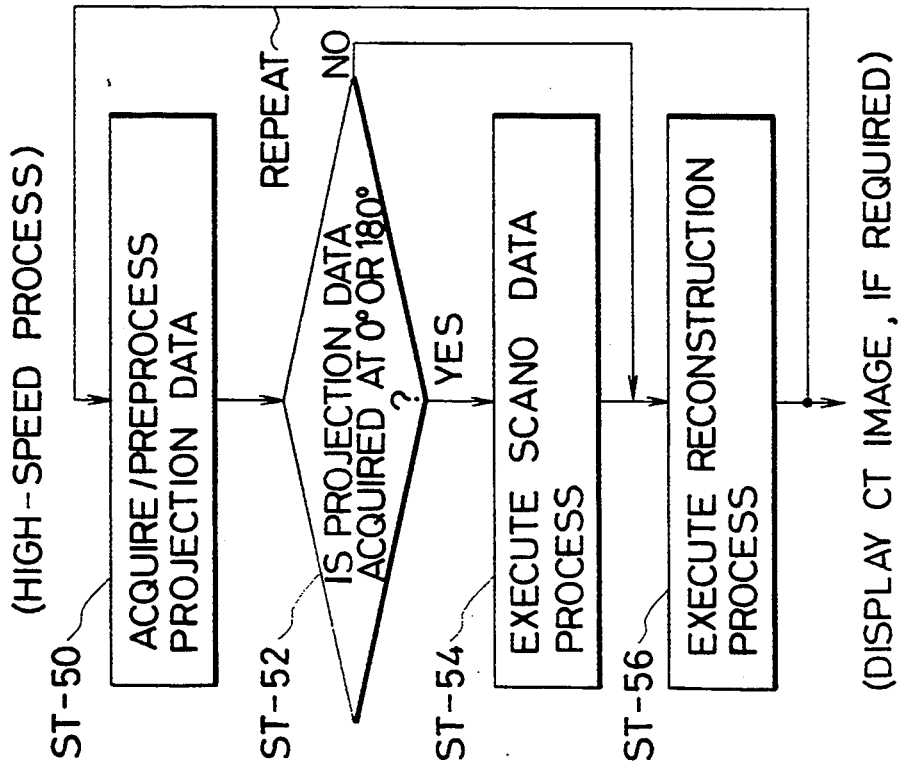
FIG. 16A is a flow chart for explaining the highspeed process operation by the fourth X-ray CT imaging system 400.

When the scanogram/CT image processing unit 90 is operable at a high speed, the entire processing operation of the fourth X-ray CT imaging system 400 is executed in accordance with a flow chart shown in FIG. 16A. At a first step ST-50 of this flow chart, the helically-scanned X-ray projection data are acquired by the X-ray scanner 2 and thereafter are preprocessed by the preprocess unit 5 under control of the main controller 56. Subsequently, a check is done as to whether or not the preprocessed projection data have been acquired at the specific projection angle 0° or 180° at a step ST-52. If YES, then the scano data process operation is carried out for these projection data acquired at the specific projection angle of 0° or 180° at a high speed at the next step ST-54. Then, the CT image reconstruction operation is performed based on these projection data at a step ST-56. A resultant CT image (not shown) reconstructed at this step ST-56 may be displayed on the display unit 4 in combination with a scanogram (not shown either) combined in the synthesizer unit 8. If NO at the step ST-52, then the process operation is jumped to the step ST-56 at which the above-described CT image reconstruction process is performed. Then, a series of the above-described highspeed process operation is repeatedly executed.

To the contrary, when the scanogram/CT image processing unit 90 is operated at a low speed, the entire processing operation of the fourth X-ray CT imaging system 400 is executed in accordance with a flow chart shown in FIG. 16B. Since the process operations from the step ST-50 to the step ST-54 are identical to those of FIG. 16A, only different process operation will be explained. That is, after the scano data process is accomplished at the step ST-54, the preprocessed X-ray projection data are once stored into a memory (not shown in detail) at the next step ST-55. Thereafter, the stored projection data are read out from the memory and are processed to reconstruct a CT image at a step ST-57.

As previously stated, according to the fourth X-ray CT imaging system 400, there are such particular advantages that the overall medical examination time for the patient can be considerably shortened even if both of the scanogram and the X-ray CT image thereof are produced, since only one helical scanning operation is required. Also, a total amount of X-ray dose given to the patient can be reduced, as compared with that of the conventional X-ray CT imaging system.

What is claimed is:

1. An X-ray CT (computerized tomographic) imaging method comprising the steps of:
   scanning a biological body under medical examination in a helical scanning mode, while relatively rotating an X-ray source around the biological body translated along a longitudinal axis of the biological body, to acquire X-ray projection image data about the helically-scanned biological body;
   selecting only X-ray projection image data acquired by an X-ray detector at a predetermined projection angle from the entire X-ray projection image data obtained at the helical-scanning step;
   processing said selected X-ray projection image data to produce a scanogram of said helically-scanned biological body; and
   reconstructing an X-ray CT image of said helically-scanned biological body based upon said entire X-ray projection image data, whereby both of said scanogram and said X-ray CT image are substantially simultaneously displayed.

2. An X-ray CT imaging method as claimed in claim 1, wherein said predetermined projection angle is selected from any one of 0°, 90° and 180° with respect to a base line located within a plane perpendicular to said longitudinal axis of the biological body.

3. An X-ray CT imaging method as claimed in claim 1, wherein said processing step includes the steps of:
   executing a curved plane/flat plane transformation with regard to said selected X-ray projection image data acquired at said predetermined projection angle to obtain plane-transformed X-ray projection image data;
   executing a highpass filtering operation with respect to the plane-transformed X-ray projection image data to obtain filtered X-ray projection image data; and
   executing a density conversion with regard to the filtered X-ray projection image data to obtain density-converted X-ray projection image data, whereby said scanogram is produced based upon the density-converted X-ray projection image data.

4. An X-ray CT imaging method as claimed in claim 3, wherein said processing step further includes the step of:
   rearranging the plane-transformed X-ray projection image data when being acquired at a second projection angle opposite to said predetermined projection angle, whereby the rearranged X-ray projection image data acquired at said second projection angle correspond to the plane-transformed X-ray projection image data acquired at said predetermined projection angle.

5. An X-ray CT (computerized tomographic) imaging method comprising the steps of:
   scanning a biological body under medical examination in a helical scanning mode, while relatively rotating an X-ray source around the biological body translated along a longitudinal axis of the biological body, to acquire X-ray projection image data about the helically-scanned biological body;
   selecting only X-ray projection image data acquired by an X-ray detector at first and second projection angles from the entire X-ray projection image data obtained at the helical-scanning step;
   processing said selected X-ray projection image data to produce first and second scanograms of said helically-scanned biological body; and
   reconstructing an X-ray CT image of said helically-scanned biological body based upon said entire X-ray projection image data, whereby both of said first and second scanograms and said X-ray CT image are substantially simultaneously displayed.

6. An X-ray CT imaging method as claimed in claim 5, wherein said first and second projection angles are 0° and 90° with respect to a base line located within a plane perpendicular to said longitudinal axis of the biological body, whereby a top-viewed scanogram is obtained as said first scanogram and a side-viewed scanogram is obtained as said second scanogram.

7. An X-ray CT (computerized tomographic) imaging method comprising the steps of:
   scanning a first portion of a biological body under medical examination by continuously projecting an X-ray beam to the first portion in a helical scanning mode, while relatively rotating an X-ray source around the biological body translated along a longitudinal axis of the biological body, to acquire first X-ray projection image data about the helically-scanned first portion of the biological body by means of an X-ray detector;
   scanning a second portion of said biological body under medical examination by intermittently projecting an X-ray beam to the second portion of the biological body at a predetermined projection angle from the X-ray tube, to acquire second X-ray projection image data about the scanned second portion of the biological body;
   processing said second X-ray projection image data to produce a scanogram of said scanned second portion of the biological body by selecting only X-ray projection image data acquired at a predetermined projection angle from the entire X-ray projection image data; and
   reconstructing an X-ray CT image of said helically-scanned biological body based upon said first X-ray projection image data, whereby both of said scanogram and said X-ray CT image are substantially simultaneously displayed.

8. An X-ray CT imaging method as claimed in claim 7, wherein said predetermined projection angle is selected from any one of 0°, 90° and 180° with respect to a base line located within a plane perpendicular to said longitudinal axis of the biological body.

9. An X-ray CT imaging method as claimed in claim 7, wherein said predetermined projection angle is selected from any two combined angles of 0°, 90° and 180° with respect to a base line located within a plane perpendicular to said longitudinal axis of the biological body.

10. An X-ray CT imaging method as claimed in claim 9, wherein said processing step includes the steps of:
    executing a curved plane/flat plane transformation with regard to said selected X-ray projection image data acquired at said predetermined projection angle to obtain plane-transformed X-ray projection image data;
    executing a highpass filtering operation with respect to the plane-transformed X-ray projection image data to obtain filtered X-ray projection image data; and
    executing a density conversion with regard to the filtered X-ray projection image data to obtain density-converted X-ray projection image data, whereby said scanogram is produced based upon the density-converted X-ray projection image data.

11. An X-ray CT imaging method as claimed in claim 10, wherein said processing step further includes the step of:
    rearranging the plane-transformed X-ray projection image data when being acquired at a second projection angle opposite to said predetermined projection angle, whereby the rearranged X-ray projection image data acquired at said second projection angle correspond to the plane-transformed X-ray projection image data acquired at said predetermined projection angle.

12. An X-ray CT (computerized tomographic) imaging system comprising:
    scanning means including an X-ray source and an X-ray detector, for scanning a biological body under medical examination in a helical scanning mode, while relatively rotating said X-ray source around the biological body translated along a longitudinal axis of the biological body, to acquire X-ray projection image data about the helically-scanned biological body;
    scano data processing means for selecting only X-ray projection image data acquired by said X-ray detector at a predetermined projection angle from the entire X-ray projection image data, and for processing said selected X-ray projection image data to produce a scanogram of said helically-scanned biological body by selecting only X-ray projection image data acquired at a predetermined projection angle from the entire X-ray projection image data;
    CT image reconstructing means for reconstructing an X-ray CT image of said helically-scanned biological body based upon said entire X-ray projection image data; and
    display means for substantially simultaneously displaying both of said scanogram and said X-ray CT image.

13. An X-ray CT imaging system as claimed in claim 12, wherein said scano data processing means includes:
    means for executing a curved plane/flat plane transformation with regard to said selected X-ray projection image data acquired at said predetermined projection angle to obtain plane-transformed X-ray projection image data;
    means for executing a highpass filtering operation with respect to the plane-transformed X-ray projection image data to obtain filtered X-ray projection image data; and
    means for executing a density conversion with regard to the filtered X-ray projection image data to obtain density-converted X-ray projection image data, whereby said scanogram is produced based upon the density-converted X-ray projection image data.

14. An X-ray CT imaging system as claimed in claim 13, wherein said scano data processing means further includes:
    means for rearranging the plane-transformed X-ray projection image data when being acquired at a second projection angle opposite to said predetermined projection angle, whereby the rearranged X-ray projection image data acquired at said second projection angle correspond to the plane-transformed X-ray projection image data acquired at said predetermined projection angle.

15. An X-ray CT imaging system as claimed in claim 12, further comprising:
    preprocessing means for preprocessing said X-ray projection image data obtained from said scanning means to produce the preprocessed X-ray projection image data to be supplied to both of said scano data processing means and said CT image reconstructing means; and
    synthesizing means for synthesizing said scanogram and said X-ray CT image to be substantially displayed on said display means.

16. An X-ray CT imaging system as claimed in claim 12, wherein said predetermined projection angle is selected from any one of 0°, 90° and 180° with respect to a base line located within a plane perpendicular to said longitudinal axis of the biological body.

17. An X-ray CT imaging system comprising:
    scanning means including an X-ray source and an X-ray detector, for scanning a biological body under medical examination in a helical scanning mode, while relatively rotating said X-ray source around the biological body translated along a longitudinal axis of the biological body, to acquire X-ray projection image data about the helically-scanned biological body by means of said X-ray detector;
    scano data processing means for selecting only X-ray projection image data acquired at first and second projection angles from the entire X-ray projection image data obtained from said scanning means, and for processing said selected X-ray projection image data to produce first and second scanograms of said helically-scanned biological body;
    CT image reconstructing means for reconstructing an X-ray CT image of said helically-scanned biological body based upon said entire X-ray projection image data; and
    display means for substantially simultaneously displaying both of said first and second scanograms and said X-ray CT image.

18. An X-ray CT imaging system as claimed in claim 17, wherein said first and second projection angles are 0° and 90° with respect to a base line located within a plane perpendicular to said longitudinal axis of the biological body, whereby a top-viewed scanogram is displayed as said first scanogram and a side-viewed scanogram is displayed as said second scanogram on said display means.

19. An X-ray CT imaging system as claimed in claim 17, wherein said scano data processing means includes:
    means for executing a curved plane/flat plane transformation with regard to said selected X-ray projection image data acquired at said predetermined projection angle to obtain plane-transformed X-ray projection image data;

means for executing a highpass filtering operation with respect to the plane-transformed X-ray projection image data to obtain filtered X-ray projection image data; and means for executing a density conversion with regard to the filtered X-ray projection image data to obtain density-converted X-ray projection image data, whereby said scanogram is produced based upon the density-converted X-ray projection image data.

20. An X-ray CT imaging system as claimed in claim 19, wherein said scano data processing means further includes:

means for rearranging the plane-transformed X-ray projection image data when being acquired at a second projection angle opposite to said predetermined projection angle, whereby the rearranged X-ray projection image data acquired at said second projection angle correspond to the plane-transformed X-ray projection image data acquired at said predetermined projection angle.

21. An X-ray CT imaging system as claimed in claim 17, further comprising:

preprocessing means for preprocessing said X-ray projection image data obtained from said scanning means to produce the preprocessed X-ray projection image data to be supplied to both of said scano data processing means and said CT image reconstructing means; and synthesizing means for synthesizing said scanogram and said X-ray CT image to be substantially displayed on said display means.

22. An X-ray CT imaging system comprising:

scanning means including an X-ray source and an X-ray detector, for continuously scanning a first portion of a biological body under medical examination in a helical scanning mode, while relatively rotating said X-ray source around the biological body translated along a longitudinal axis of the biological body, to acquire first X-ray projection image data about the helically-scanned first portion of the biological body by said X-ray detector, and also for scanning a second portion of said biological body by intermittently projecting an X-ray beam of said X-ray source to the second portion of the biological body, to acquire second X-ray projection image data about the scanned second portion of the biological body;

scano data processing means for processing said second X-ray projection image data to produce a scanogram of said scanned second portion of the biological body by selecting only X-ray projection image data acquired at a predetermined projection angle from the entire X-ray projection image data;

CT image reconstructing means for reconstructing an X-ray CT image of said helically-scanned biological body based upon said entire X-ray projection image data; and display means for substantially simultaneously displaying both of said scanogram and said X-ray CT image.

23. An X-ray CT imaging system as claimed in claim 22, wherein said predetermined projection angle is selected from any one of 0°, 90° and 180° with respect to a base line located within a plane perpendicular to said longitudinal axis of the biological body.

24. An X-ray CT imaging system as claimed in claim 22, wherein said scano data processing means includes:

means for executing a curved plane/flat plane transformation with regard to said selected X-ray projection image data acquired at said predetermined projection angle to obtain plane-transformed X-ray projection image data;

means for executing a highpass filtering operation with respect to the plane-transformed X-ray projection image data to obtain filtered X-ray projection image data; and means for executing a density conversion with regard to the filtered X-ray projection image data to obtain density-converted X-ray projection image data, whereby said scanogram is produced based upon the density-converted X-ray projection image data.

25. An X-ray CT imaging system as claimed in claim 24, wherein said scano data processing means further includes:

means for rearranging the plane-transformed X-ray projection image data when being acquired at a second projection angle opposite to said predetermined projection angle, whereby the rearranged X-ray projection image data acquired at said second projection angle correspond to the plane-transformed X-ray projection image data acquired at said predetermined projection angle.

26. An X-ray CT imaging system as claimed in claim 22, further comprising:

preprocessing means for preprocessing said X-ray projection image data obtained from said scanning means to produce the preprocessed X-ray projection image data to be supplied to both of said scano data processing means and said CT image reconstructing means; and synthesizing means for synthesizing said scanogram and said X-ray CT image to be substantially displayed on said display means.

* * * * *